US005845269A

United States Patent [19]

Körtge et al.

[11] Patent Number: 5,845,269

[45] Date of Patent: Dec. 1, 1998

[54] FUZZY CONTROL SYSTEM, PARTICULARLY FOR DOSE RATE CONTROL IN AN X-RAY DIAGNOSTICS APPARATUS

[75] Inventors: Detlef Körtge, Nürnberg; Michael Franz, Erlangen, both of Germany

[73] Assignee: Siemens Aktiengesellschaft, Munich, Germany

[21] Appl. No.: 714,160

[22] PCT Filed: Mar. 15, 1995

[86] PCT No.: PCT/DE95/00363

§ 371 Date: Sep. 23, 1996

§ 102(e) Date: Sep. 23, 1996

[87] PCT Pub. No.: WO95/25990

PCT Pub. Date: Sep. 28, 1995

[30] Foreign Application Priority Data

Mar. 21, 1994 [DE] Germany ............................ 9404768 U

[51] Int. Cl.[6] ........................................................ G06F 9/44

[52] U.S. Cl. ................................ 706/3; 706/903; 706/924

[58] Field of Search ................................ 395/50, 51, 61, 395/900; 706/3, 903, 924

[56] References Cited

U.S. PATENT DOCUMENTS 5,148,032 9/1992 Hernandez .............................. 378/108

FOREIGN PATENT DOCUMENTS 0 063 644 11/1982 European Pat. Off. .
0 362 427 4/1990 European Pat. Off. .
0 385 387 9/1990 European Pat. Off. .
0 405 149 1/1991 European Pat. Off. .
0 429 680 6/1991 European Pat. Off. .
2 608 416 6/1988 France .

OTHER PUBLICATIONS

Proceedings of the IEEE 1990 Custom Integrated Circuits Conference, Dettloff et al, "A VLSI Fuzzy Logic Interference Engine for Real–Time Processng Control", May 1989.

Xiang et al., "The Processing and Recognition of X–Rays of Spine Tumor", 9th International Conference on Pattern Recognition, Nov. 1988, Italy, 14–17.

*Primary Examiner*—George B. Davis
*Attorney, Agent, or Firm*—Hill & Simpson

[57] ABSTRACT

A fuzzy control system, particularly for dose rate control in an X-ray diagnostics apparatus, such a control system converting input signals into output signals. A first and a second individual module are provided, whereby respectively at least two input signals can be supplied to the first and to the second individual module for generating an output signal. Compared to a fuzzy control system that does not comprise these individual modules, the rule base becomes smaller, only input conditions that have influence on the individual module need be provided with rules, so that a simple check of the rules for completeness is assured.

9 Claims, 24 Drawing Sheets

| Type | Size | | | | | |
| --- | --- | --- | --- | --- | --- | --- |
| weight | | very small | small | average | big | very big |
| | very light | very thin | very thin | very thin | very thin | very thin |
| | light | normal | normal | normal | normal | normal |
| | normal | fat | fat | fat | normal | normal |
| | heavy | very fat | very fat | fat | normal | normal |
| | very heavy | very fat | very fat | fat | normal | normal |

FIG 10

| Location | X-Axis | | | | | | |
|---|---|---|---|---|---|---|---|
| | | head | chest | heart | stomach | thigh | calf |
| Y-Axis | left arm | nothing | arm | arm | arm | nothing | nothing |
| | left side | nothing | chest | chest | stomach | thigh | calf |
| | middle | head | chest | heart | stomach | nothing | nothing |
| | right side | nothing | chest | chest | stomach | thigh | calf |
| | right arm | nothing | arm | arm | arm | nothing | nothing |

FIG 14

| Exposure points | Location | | | | | | | | |
|---|---|---|---|---|---|---|---|---|---|
| Type | | nothing | calf | arm | chest | thigh | heart | stomach | head |
| | very thin | average | very very small | very small | very small | very small | very small | very small | big |
| | thin | average | small | very small | small | small | small | small | big |
| | normal | average | small | very small | small | small | small | big | very big |
| | fat | average | small | small | small | big | big | very big | very big |
| | very fat | average | big | small | big | big | big | extremely big | very very big |

FIG 18

| Compensation factor 1 | Location | | | | | | | | |
|---|---|---|---|---|---|---|---|---|---|
| | | nothing | calf | arm | chest | thigh | heart | stomach | head |
| R-LAO | upper right | very very small | average | average | average | average | average | average | average |
| | slanting top right | very very small | average | average | big | average | big | big | small |
| | right | very very small | average | average | very big | average | very big | very big | very small |
| | slanting bottom right | very very small | average | average | big | average | big | big | small |
| | bottom | very very small | average | average | average | average | average | average | average |
| | slanting bottom left | very very small | average | average | big | average | big | big | small |
| | left | very very small | average | average | very big | average | very big | very big | very small |
| | slanting top left | very very small | average | average | big | average | big | big | small |
| | upper left | very very small | average | average | average | average | average | average | average |

FIG 22

| Compensation factor 1 | Location | | | | | | | | |
|---|---|---|---|---|---|---|---|---|---|
| | | nothing | calf | arm | chest | thigh | heart | stomach | head |
| k-k | negative very big | small | big | big | big | big | big | big | average |
| | negative big | small | average | average | average | average | average | average | small |
| | negative small | small | small | small | small | small | small | small | small |
| | zero | small | small | small | small | small | small | small | small |
| | postive small | small | small | small | small | small | small | small | small |
| | positive big | small | average | average | average | average | average | average | small |
| | positive very big | small | big | big | big | big | big | big | average |

FIG 26

| Rule base | | | | | | | | | | |
|---|---|---|---|---|---|---|---|---|---|---|
| Corr. 1 | | minimal | extremely small | very very small | very small | small | big | very big | very very big | extremely big |
| | very very small | minimal | minimal | minimal | minimal | minimal | minimal | minimal | minimal | minimal |
| | very small | minimal | minimal | extremely small | extremely small | extremely small | very very small | very very small | very very small | very small |
| | small | minimal | extremely small | extremely small | very very small | very small | very small | small | big | big |
| | average | minimal | extremely small | very very small | very small | small | big | very big | very very big | extremely big |
| | big | minimal | extremely small | very small | small | big | very very big | very very big | gigantic | gigantic |
| | very big | minimal | very very small | very small | small | very very big | extremely big | gigantic | gigantic | gigantic |
| | very very big | minimal | very very small | small | very big | extremely big | gigantic | gigantic | gigantic | gigantic |

FIG 30

| Exposure points 3 | Exposure Points 2 | | | | | | | | | |
|---|---|---|---|---|---|---|---|---|---|---|
| Compen-sation factor | | minimal | extremely small | very very small | very small | small | big | very big | very very big | extremely big |
| | small | minimal | extremely small | very very small | very small | small | big | very big | very very big | extremely big |
| | average | minimal | very very small | very small | small | big | extremely big | extremely big | extremely big | extremely big |
| | big | minimal | very small | small | very big | very big | extremely big | extremely big | extremely big | extremely big |

FUZZY CONTROL SYSTEM, PARTICULARLY FOR DOSE RATE CONTROL IN AN X-RAY DIAGNOSTICS APPARATUS

BACKGROUND OF THE INVENTION

1. Field of the Invention

The present invention relates generally to a fuzzy logic control system which uses multiple input modules to reduce the rule base.

2. Description of the Related Art

Fuzzy control systems can be divided into a fuzzification domain, a domain of a rule base and inference formation and into a defuzzification domain.

In a fuzzy control system, the input values are referred to as sharp input values. In the fuzzification, the sharp input values are converted into a fuzzy value in order to be further-processed in the fuzzy control system. Each input of the fuzzy control system is referenced with a linguistic variable, for example body size or weight of a patient. An input range in which the sharp input value can vary is defined for this variable. The input range is subdivided into sub-ranges, what are referred to as the fuzzy sets. Each of these fuzzy sets contains a characteristic designation. A linguistic variable, for example "weight", can be divided into the ranges small, average, big. Each fuzzy set is presented by a function. The membership degree ($\mu$) with which a sharp input value is located in the range of a fuzzy set is determined with this function. The result of the determination of membership degrees is not a boolean value but ranges between 0 and 1.

The system behavior is determined in the domain of the rule base and inference formation. The rule base represents a collection of verbally formulated rules that link the input and output fuzzy sets. Given two inputs and one output, the rules have the following form:

when $A_i=a_{im}$ and $A_j=a_{jm}$, then $B_k=B_{kn}$ when $A_i=a_{im}$ or $A_j=a_{jm}$, then $B_k=B_{kn}$ $A_i$ or, respectively, $A_j$ represent linguistic input variables and $a_{im}$ or, respectively, $a_{jm}$ represent a fuzzy set of the linguistic input variables $A_i$ or, respectively, $A_j$. $B_k$ stands for a linguistic output variable with the fuzzy set $b_{kn}$.

A rule determines what output fuzzy sets should be weighted by what input fuzzy sets. A membership value is assigned to an output fuzzy set in the weighting. An output set can only be weighted with one value. Given more than one input fuzzy set, the resultant weighting factor must be determined first. To that end, the inputs can be operated with a number of operators.

The inference formation implements the weighting of the output set. Two methods are thereby possible. The first is to cut the output fuzzy set off at the height of the resultant membership degree. This is thereby refer red to as the "min-max method". The second method would be to proportionally reduce the output fuzzy set from its normal size to the height that corresponds to the identified membership degree. This is the "max-prod method".

In the defuzzification domain, the weighted output fuzzy sets obtained in the inference formation are brought into a form as a system result that can be understood by the "non-fuzzy world". Fuzzification methods are the maximum method, the left-(right-)max method and the center of gravity method. Which method is selected is entirely dependent on how the fuzzy result is to be interpreted.

When the combination in which the input values are adjacent is not taken into account in a fuzzy control system, then each combination must be considered to be possible. Given, for example, six different inputs with a total of 37 fuzzy sets, 47,250 rules must be erected. Due to the multitude of rules to be erected, the risk is high that some rules will not have been formulated. A check must be carried out to see whether all rules were in fact formulated, this resulting in a high time expenditure.

European published application EP-A1-0 063 644 discloses to set the exposure parameters (voltage/current, Mas product, the blackening, the measuring field) allocated to organ or group of organs. The ultimate setting of these parameters ensues under the influence of radiation.

French published application FR-A1-2 608 416 discloses an exposure control of an X-ray diagnostics apparatus wherein logarithmic characteristics are employed for the linearization of the control circuit. The data acquisition for the linearization of the control circuit ensues under the influence of radiation.

European published application EP-A1-0 362 427 discloses an X-ray diagnostics system with a detector for the average image brightness that, further, comprises a control means with a memory for a plurality of datasets corresponding to the respectively displayed body parts. A selection means automatically selects the respective dataset corresponding to the respective body part and a stored absorption profile on the basis of a pattern recognition.

The reference "Proceedings of the IEEE 1989 Custom Integrated Circuits Conference", 15 May 1989, USA, pp. 12.4.1 through 12.4.5, W. Detloff et al., a VLSI fuzzy logic inference engine for real-time process control" discloses a fuzzy control system with individual modules.

SUMMARY OF THE INVENTION

An object of the invention is to implement an X-ray diagnostics apparatus in such a way that the starting values for the dose rate control are obtained without the influence of radiation.

This and other objects and advantages of the invention are achieved by an X-ray diagnostics apparatus with a fuzzy control system for dose rate control, whereby the start values for the dose rate control are determined from signals specifying the type of examination subject and/or representing the position of a bearing mechanism in a plane and/or representing the alignment of the exposure unit.

An advantage of the invention is that the starting values for the dose rate control are determined in dependence on data related to the subject of examination and/or apparatus data.

It is advantageous if inputs or, respectively, input signals of the fuzzy control system are distributed onto individual modules that can be considered to be discrete fuzzy systems. Due to the reduced number of inputs for an individual module, the rule base becomes smaller. Only input conditions that influence the individual module must be covered with rules. When the number of inputs per individual module is limited to two, the rule base per output can be represented by a matrix. This form of presentation allows a simple checking of the rules for completeness, prevents the erection of contradictory rules and the multiple erection of rules. Moreover, an output of an individual module can be presented as a surface in three-dimensional space dependent on its inputs. The system behavior can be illustrated by this means; moreover, the graphic presentation enables the rapid checking of the system behavior for correct function.

Further advantages and details of the invention derive from the following description of an exemplary embodiment, wherein an X-ray diagnostics apparatus with a fuzzy control system has the signals specifying the type of examination subject supplied to the input of a first individual module. The signals representing the weight of the examination subject can be supplied to a first input of the first individual module and the signals representing the size of the examination subject can be supplied to a second input. Signals representing the position of a bearing mechanism in a plane can be supplied to the input of a second individual module for location classification. The output signal of the first and second individual module can be supplied to a third individual module for first exposure point determination. The output signal of the second individual module and a signal corresponding to an angle of inclination of the pick-up unit of the X-ray diagnostic apparatus can be supplied to a fourth individual module. The output signal of the second individual module and the signal representing a rotational angle of the pick-up unit can be supplied to a fifth individual module. The output signal of the third and of the fourth individual module can be supplied to a sixth individual module for the second exposure point determination. The output signal of the fifth and of the sixth individual module can be supplied to a seventh individual module, and whereby the output signal of the seventh individual module is utilized for control of the radiation transmitter of the pick-up unit.

BRIEF DESCRIPTION OF THE DRAWINGS

FIGS. 3, 4, 5 and 6 are graphs and a table showing exemplary embodiments of an input and output fuzzy set as well as a rule base for type classification of the fuzzy control system of FIG. 2;

FIGS. 7, 8, 9 and 10 are graphs, a diagram and a table showing exemplary embodiments of an input and output fuzzy set as well as a rule base for location classification of the fuzzy control system of FIG. 2;

FIGS. 11, 12, 13 and 14 are graphs and a table showing exemplary embodiments of an input and output fuzzy set as well as a rule base for the first exposure point determination of the fuzzy control system of FIG. 2;

FIGS. 15, 16, 17 and 18 are graphs and a table showing exemplary embodiments of an input and output fuzzy set as well as a rule base for compensation of the orbital motion of a fuzzy control system of FIG 2;

FIGS. 19, 20, 21 and 22 are graphs and a table showing exemplary embodiments of an input and output fuzzy set as well as a rule base for the compensation of the angulation of the fuzzy control system of FIG. 2;

FIGS. 23, 24, 25 and 26 are graphs and a table showing exemplary embodiments of an input and output fuzzy set as well as a rule base for the second exposure point determination of the fuzzy control system of FIG. 2;

FIGS. 27, 28, 29 and 30 are graphs and a table showing exemplary embodiments of an input and output fuzzy set as well as a rule base for the third exposure point determination of the fuzzy control system of FIG. 2.

DETAILED DESCRIPTION OF THE PREFERRED EMBODIMENTS

Figure 1:
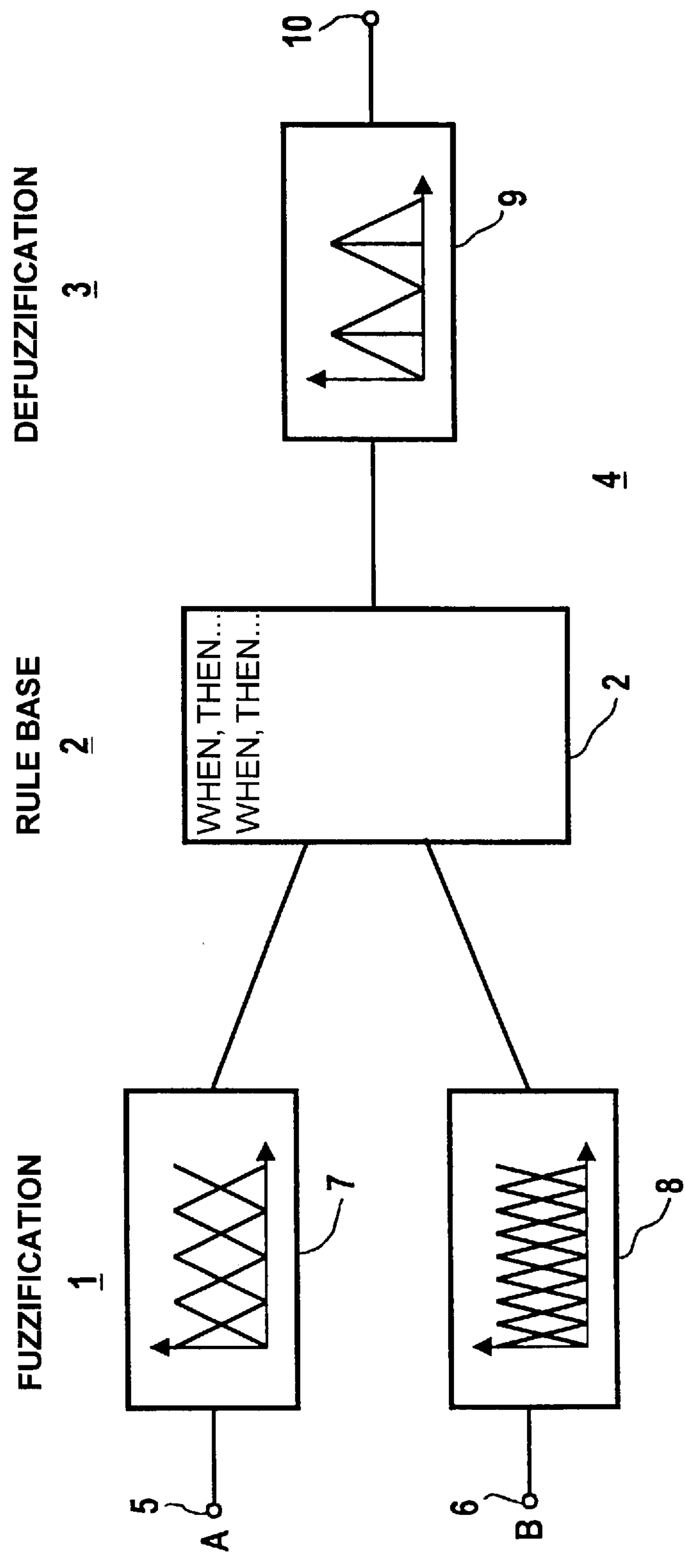
FIG. 1 is a block diagram showing an exemplary embodiment of an individual module of a fuzzy control system of the invention.

In FIG. 1, reference character 1 indicates a fuzzification domain, reference character 2 indicates a rule base and reference character 3 indicates a defuzzification domain. According to the invention, the individual module 4 shown by way of example in FIG. 1 is only supplied with a limited number of input signals (A,B), so that the rule base need only be provided with rules that influence this individual module 4. As shown, two inputs A and B are preferably allocated to the individual module 4. The respectively defined input ranges 7 and 8 of the inputs 5 and 6 are operated in the rule base 2, and an output range 9 is defined by defuzzification, so that a control signal can be derived at the output 10. When the number of inputs 5 and 6 per individual module is limited to two, then the rule base 2 per output 10 can be represented by a matrix. This form of presentation allows a simple check of the rules for completeness and prevents the erection of contradictory and redundant rules. Depending on its inputs 5 and 6, moreover, an output can be represented as surface in the three-dimensional space. This illustrates the system behavior and, due to the graphic presentation, enables a fast check of the system behavior for correct operation.

Figure 2:
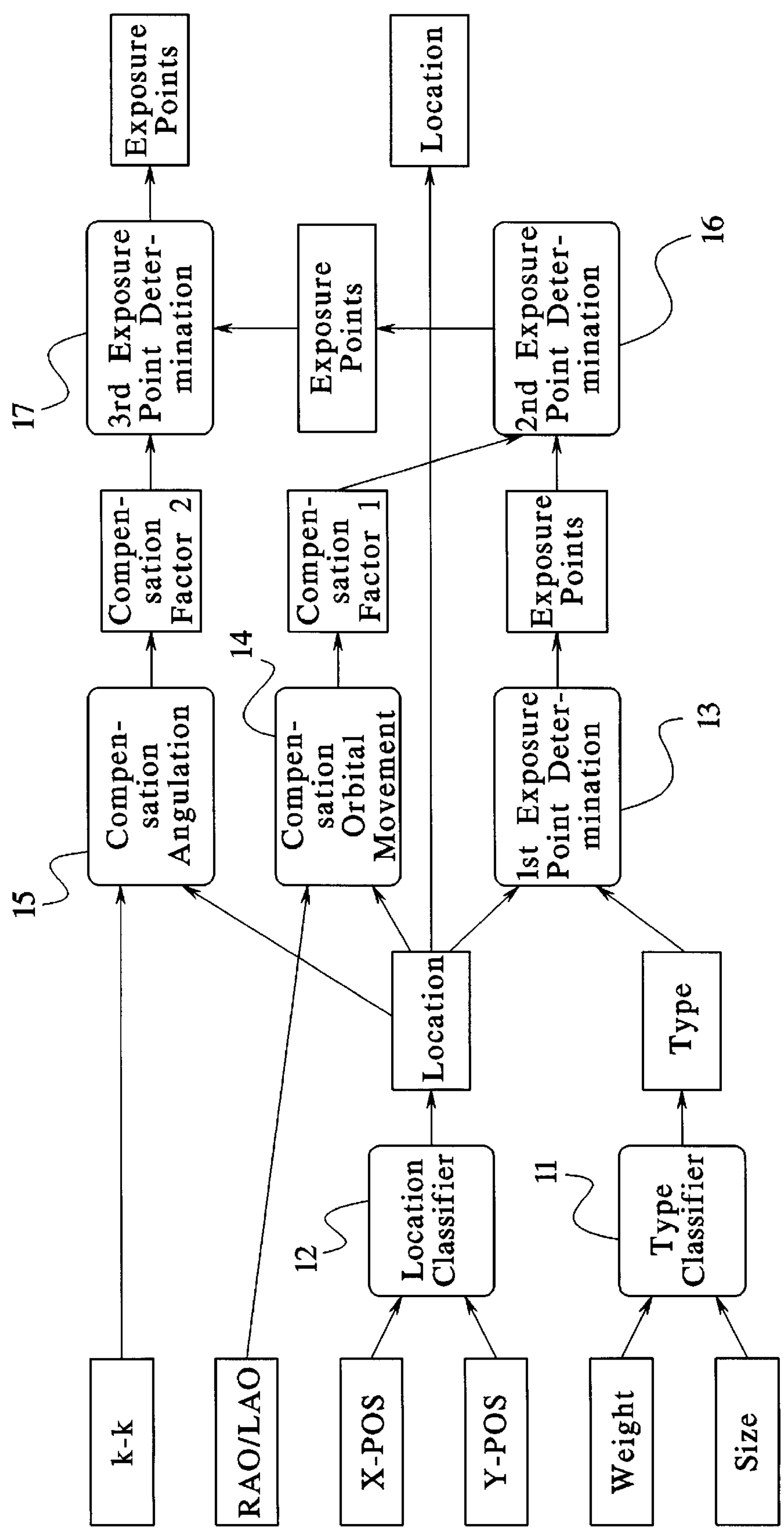
FIG. 2 is a block diagram showing an exemplary embodiment of a fuzzy control system of the invention.
Figure 3:
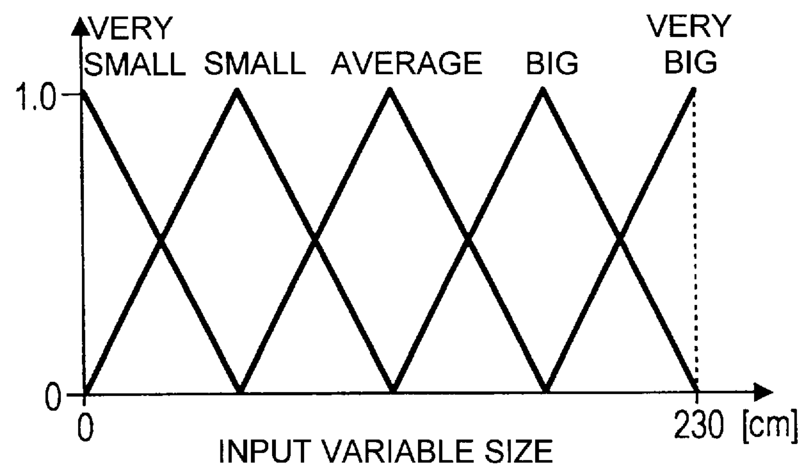
Figure 4:
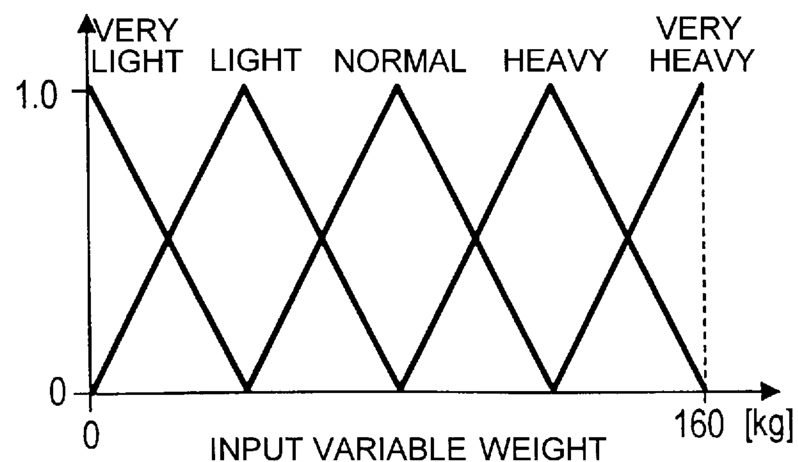
Figure 5:
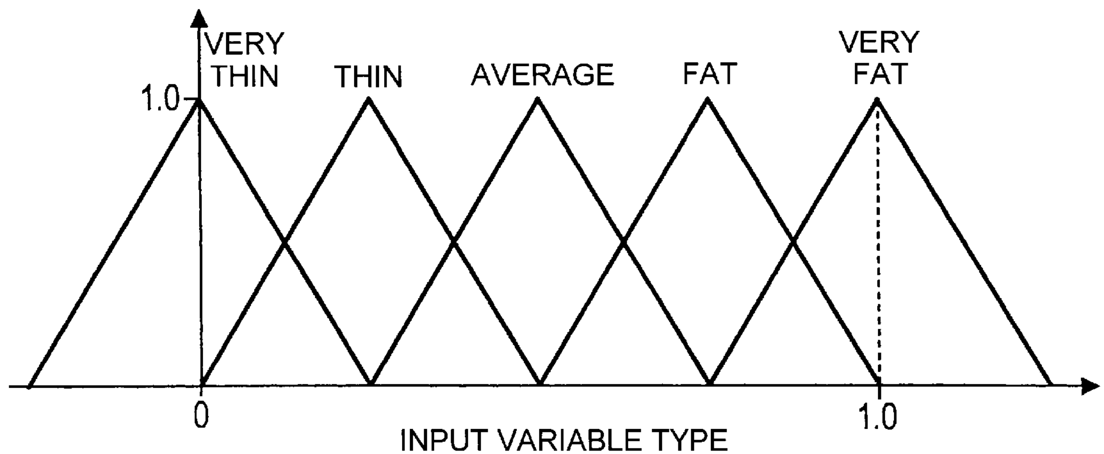

It can be seen from FIG. 2 that two inputs of the fuzzy control system are combined in an individual module for the formation of an intermediate result. According to the invention, a plurality of individual are utilized until a final result is formed by the last individual module on the basis of all input signals. A first individual module is identified with reference character 11 as a type classifier. For example, the signals representing the weight and the size of an examination subject 21 (as shown in FIG. 30) are supplied to this first individual module 11 as input parameters (FIGS. 3 and 4). The first individual module 11 thus serves the purpose of identifying the physical stature. To what extent the data of the examination subject 21 can be allocated to the various body types can thus be estimated with the result of the type classification. The body of the examination subject 21 can thus be allocated to various body classes. The degree of coincidence of the body of the examination subject 21 with a pre-identified body type is represented with a membership value for each body type. The sum of all membership values can thereby not become greater than 1. What is referred to as the Quetlet quotient can be utilized as guideline for a "normal" body type. The Quetlet quotient states that, given a normal body weight, the quotient of body weight and physical height in meters to the square must lie between 23 and 25. A correspondingly smaller or bigger quotient value can be assumed given the other body classes such as very thin, thin, average, fat, very fat (see FIG. 5). These quotients are used to erect the rules, i.e. the rule base (shown in FIG. 6). It must be taken into consideration that a more detailed description of the body of the examination subject 21 cannot ensue with only two input parameters. Potential body thicknesses at specific locations, for example forearm or stomach, cannot be identified. Only a rough classification is thus carried out, this only conveying an overall impression. The physical stature represents an absolute dimension that is viewed as average body thickness. This enables an adaptation of the exposure points not only to fat and thin examination subjects 21 of the same height but also to examination subjects 21 who have a different physical height but the same physical stature. In addition to FIGS. 5 and 6, FIGS. 3 and 4 are also referenced to the first individual module 11, these showing the input fuzzy sets. FIG. 3 shows a input fuzzy set with respect to the input variable "size" and FIG. 4 shows an input fuzzy set with respect to "weight".

Figure 7:
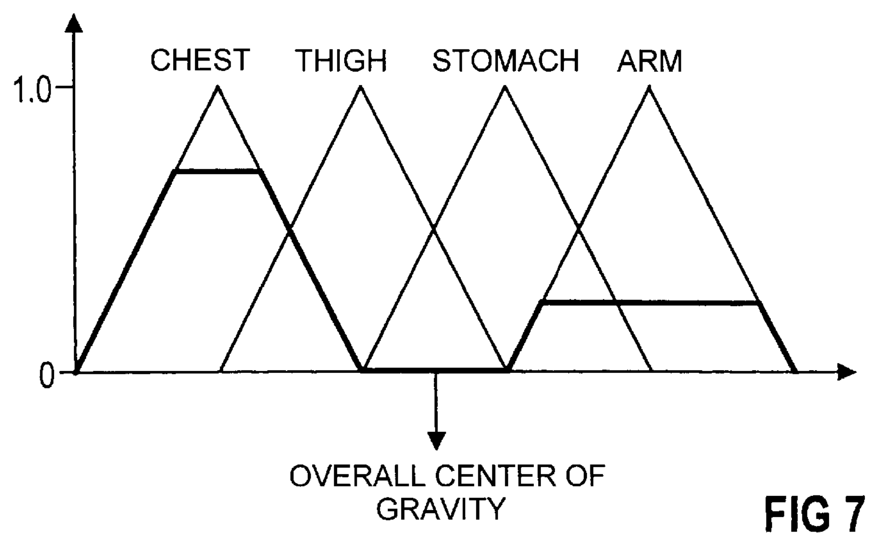

The X and Y coordinates of a radiation transmitter 22 are supplied to a second input module 22. The X coordinate is thereby a relative particular about the length of the examination subject 21 and can assume values between 0 and 1. The Y coordinate is a relative particular about the width of the examination subject 21 and can likewise assume values between 0 and 1. The position of the radiation transmitter 22 is preferably recited relative to the position of the table 18, whereby the position particulars are normed with the dimensions of the body of the examination subject 21. The location classifier serves the purpose of identifying the body region over which the radiation transmitter 22 is located or, respectively, that would be covered in an X-ray exposure. This is thereby based on an Xray transmitter 22 that is not inclined or tilted and that resides vertically above the examination subject 21 or, respectively, table 18. The fuzzy result of the location classifier indicates the degrees to which the various body regions are affected by the radiological examination. Two different information values can be formed from this fuzzy result. First, a representative exposure point value is indicated for the examination region. Second, the body part affected by the examination is output. The location classification for the determination of exposure points ensues on the basis of fuzzification according, for example, to the center of gravity method. In order to avoid output errors in the fuzzification, the sets of linguistic output variables are sorted according to the amount of their allocated exposure points. Only two sets have a membership value greater than zero in the fuzzification. What is thereby avoided is that the center of gravity determination has a result that could also be the result of some other fuzzy set pair. FIG. 7 is particularly referenced with respect thereto. A value can be formed from the fuzzy sets "chest" and "arm" that could also have been formed from the fuzzy sets "thigh" and "stomach". The "thigh" and "stomach", however, require a different number of exposure points than the "chest" or "arm". The defuzzification with the "left-max method" is applied as output value in the location classification. The fuzzy set with the highest membership value is the result that indicates the location of the examination. Both output values of the location classification a redetermined by the input fuzzy sets shown in FIG. 8 and output fuzzy sets shown in FIG. 9 as well as by the rule base shown in FIG. 10.

Figure 11:
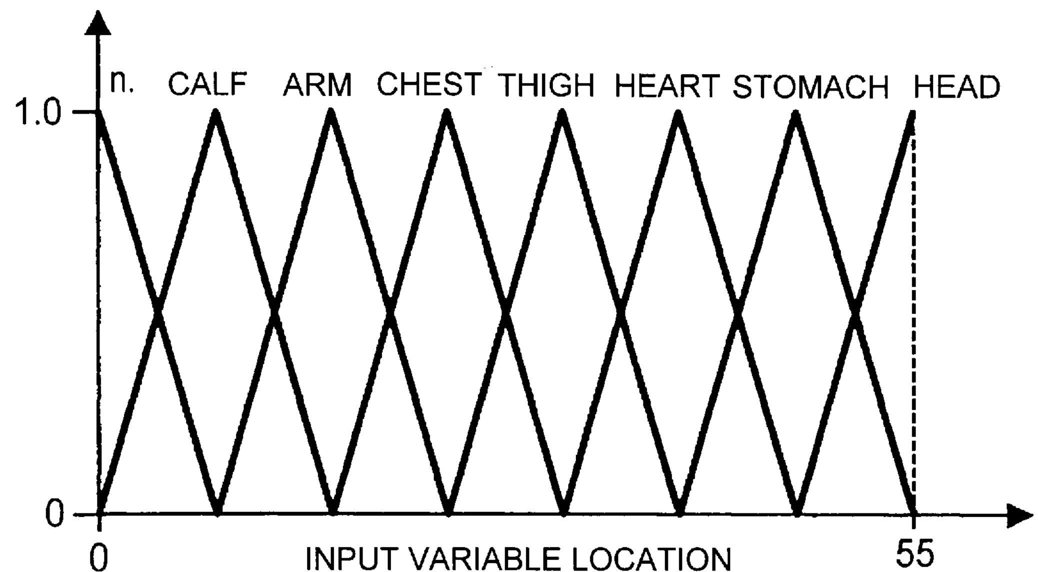
Figure 12:
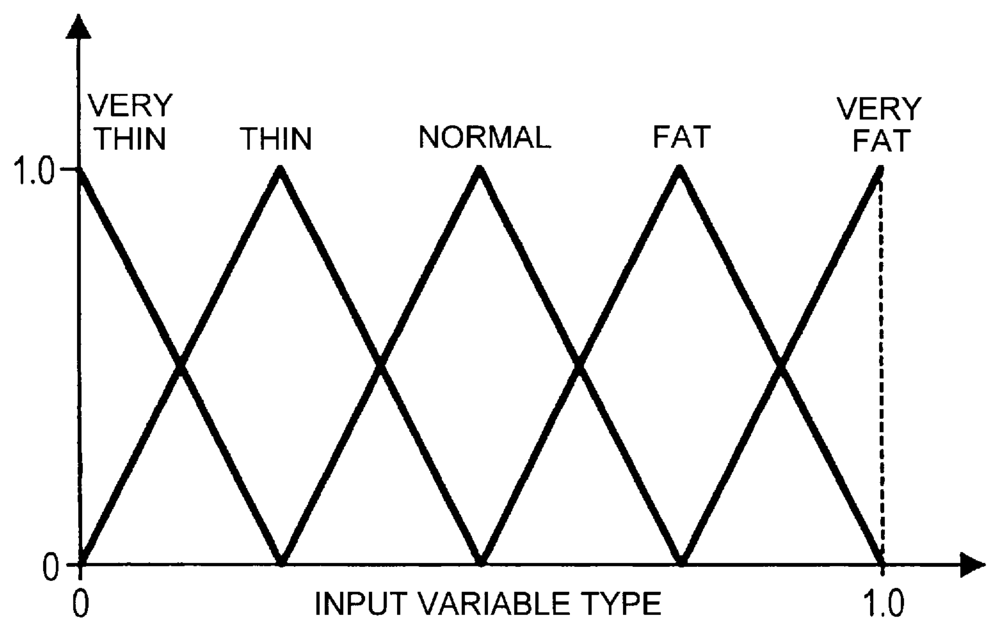
Figure 13:
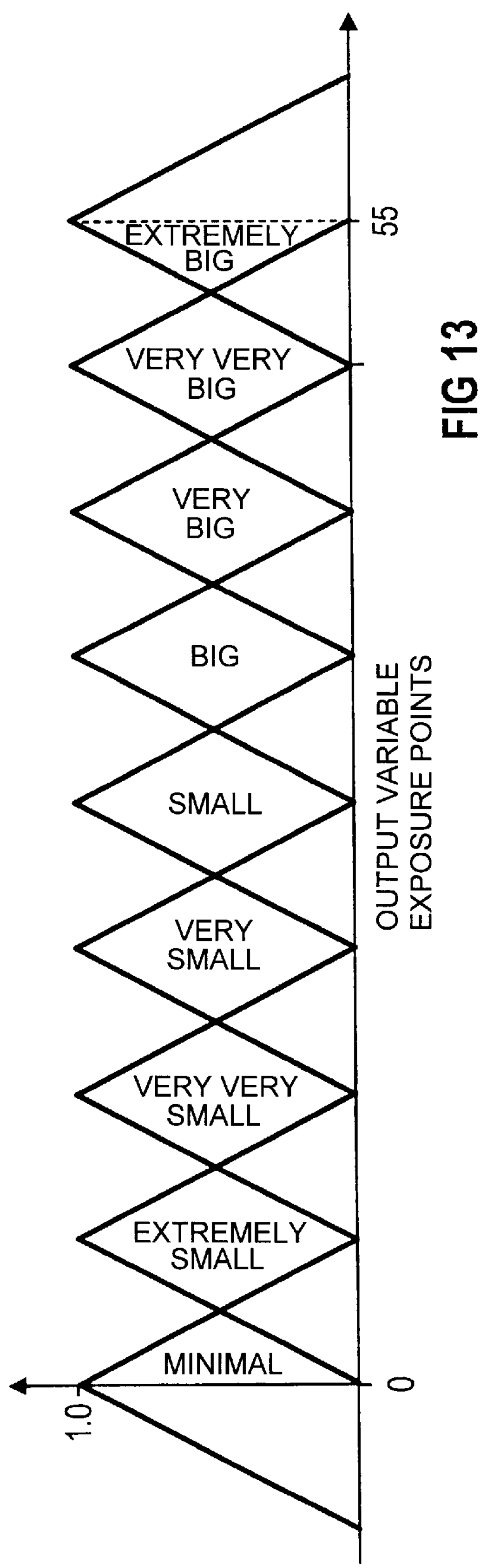

A third individual module 13 serves for the first exposure point determination. As input parameters, this third individual module 13 is supplied with signals pertaining to the body type, i.e. output signals of the first individual module 11, and with signals about the body part or, respectively, organ over which the radiation transmitter is 22 located, i.e. output signals of the second individual module 12. The majority of the exposure table is converted with this third individual module 13. The necessary exposure point value is output dependent on the body part or organ and estimated physical stature. A transirradiation that is perpendicular relative to the examination subject 21 thereby forms the basis, i.e. a frontal exposure. FIGS. 11 and 12 show the input fuzzy sets of the third individual module 13 as, first, an input variable with respect to the location and, second, with respect to the type. The output variable of the exposure points is shown as the output fuzzy set in FIG. 13. The corresponding rule base may be derived from FIG. 14.

A fourth individual module 14 is provided for the compensation of the orbital movement. As input parameters, this fourth individual module 14 is supplied with the rotational angle RAO/LAO of the radiation transmitter 21 and the organ or body part over which the radiation transmitter 21 is located, i.e. the output signal of the second individual module 12. A first compensation factor is formed as output parameter. The body thickness to be transirradiated changes due to the rotation of the radiation transmitter 22 around the longitudinal axis 20 of the examination subject 21, see FIG. 8. This results therein that the corresponding number of exposure points must be adapted to the body thickness. It is thereby assumed that the affected body part or, respectively, organ remains the same. Dependent on the rotational angle (orbital movement: rotation around the longitudinal axis of the body (RAO/LAO); angulation: slope of the beam path relative to the head or foot (cranial/caudal [sic])) and affected body region, the fourth individual module 14 determines the factor with which the exposure point value should be corrected. This is particularly important when the trunk of the examination subject 21 is to be subjected to an examination. Given examinations of the head, the arms and legs, a corresponding correction is of subordinate significance since these body parts also retain approximately the same thickness given rotation of the radiation transmitter 22, this at most affecting the determination of the exposure points. This applies to the orbital movement when the subject is located in the isocenter.

Figure 15:
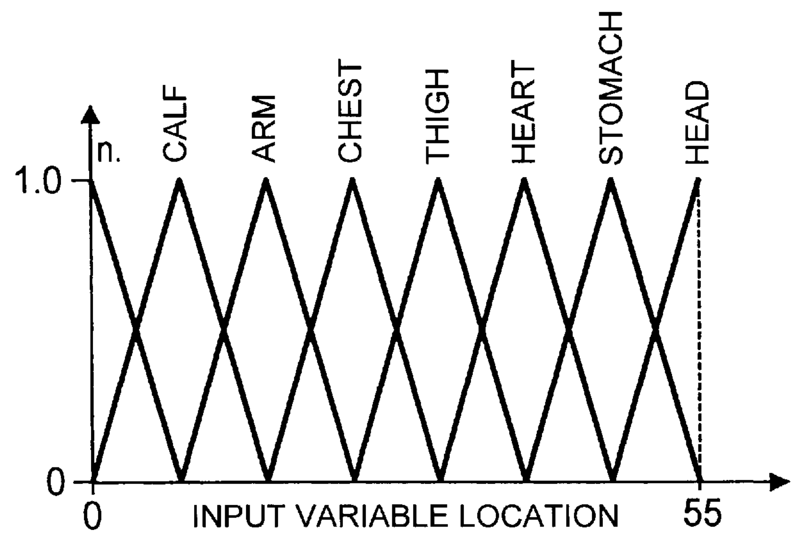
Figure 16:
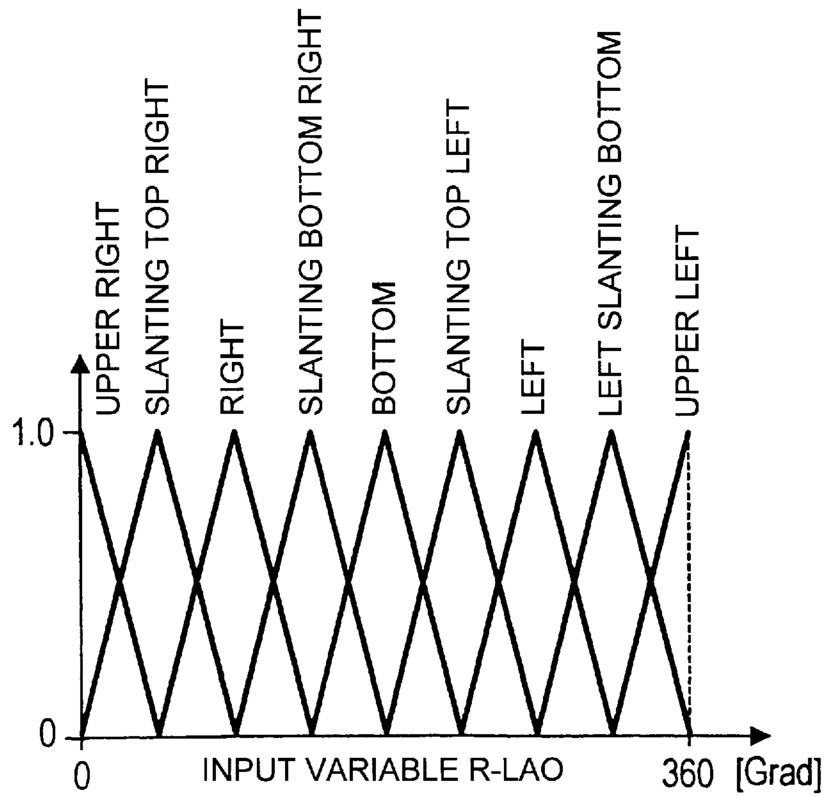
Figure 17:
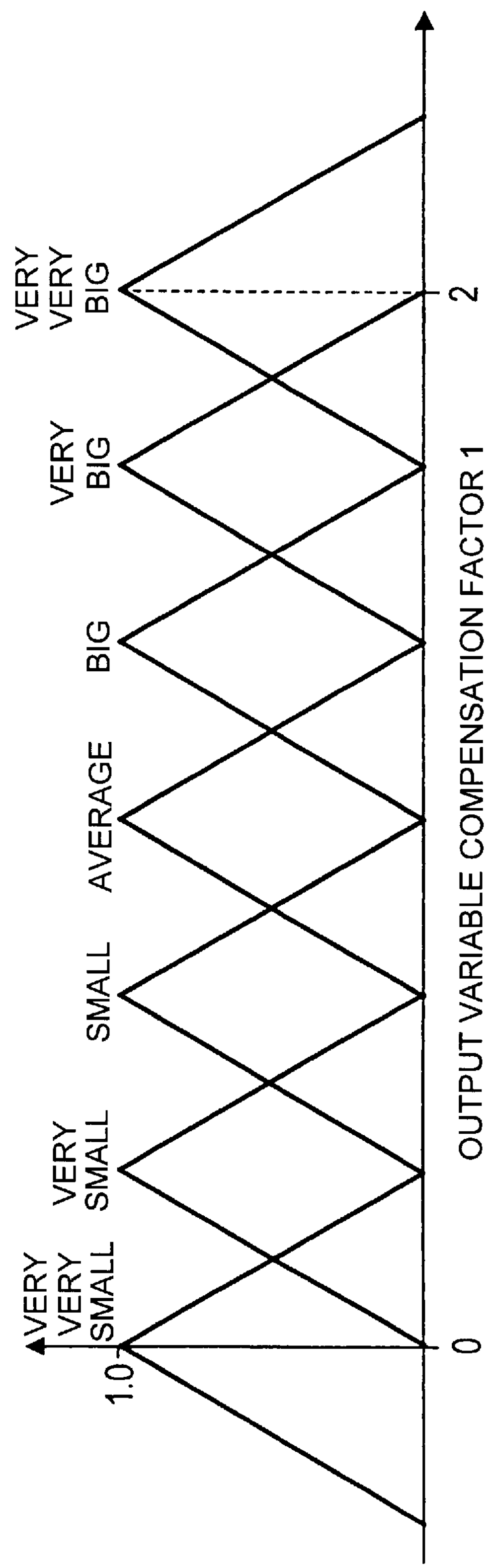

FIGS. 15 and 16 shows the input fuzzy sets, FIG. 17 the output fuzzy sets and FIG. 18 the rule base of the fourth individual module 14.

Figure 19:
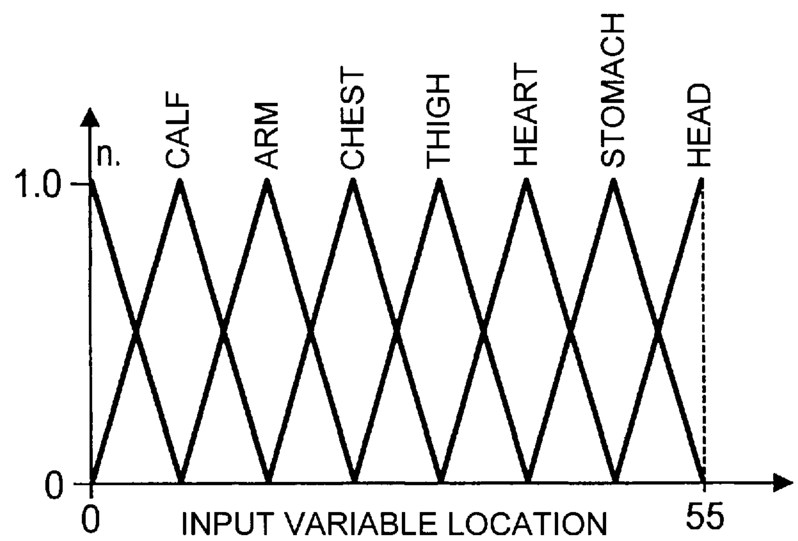
Figure 20:
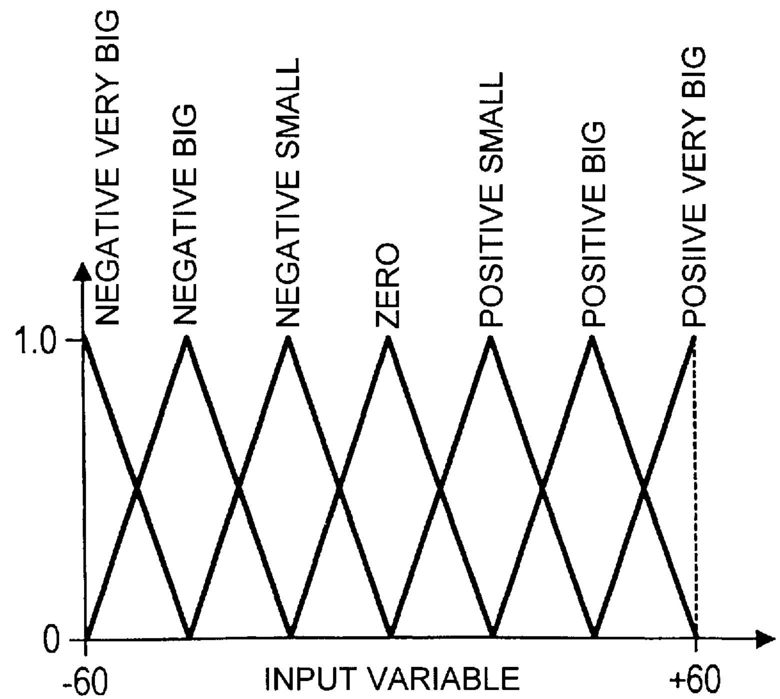
Figure 21:
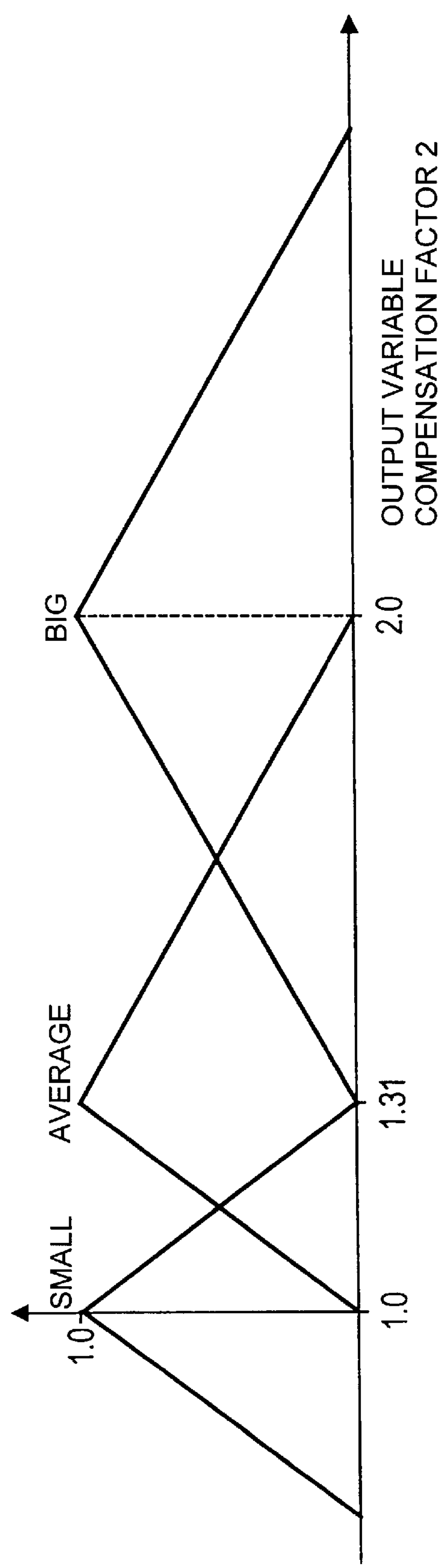

A fifth individual module 15 serves for the compensation of the angulation. As input parameters, this fifth individual module 15 is supplied with the angle of inclination k—k (cranial—caudal [sic]) of the radiation transmitter 22 and the location or, respectively, the organ or body part over which the radiation transmitter 22 is located, i.e. the output signal of the second individual module 12. A second compensation factor is formed as output parameter. The body thickness to be transirradiated likewise changes due to the inclination of the radiation transmitter 22 relative to the head or the legs of the examination subject 21. This results therein that the corresponding number of exposure points must be matched to the body thickness. It is thereby assumed that the affected body part or, respectively, organ remains the same. Dependent on the inclination angle k—k and the affected body region, this fifth individual module 15 determines the factor with which the exposure point value must be corrected. FIGS. 19 and 20 show the input fuzzy sets, FIG. 21 the output fuzzy sets and FIG. 22 the rule base of the fifth individual module 15.

Figure 23:
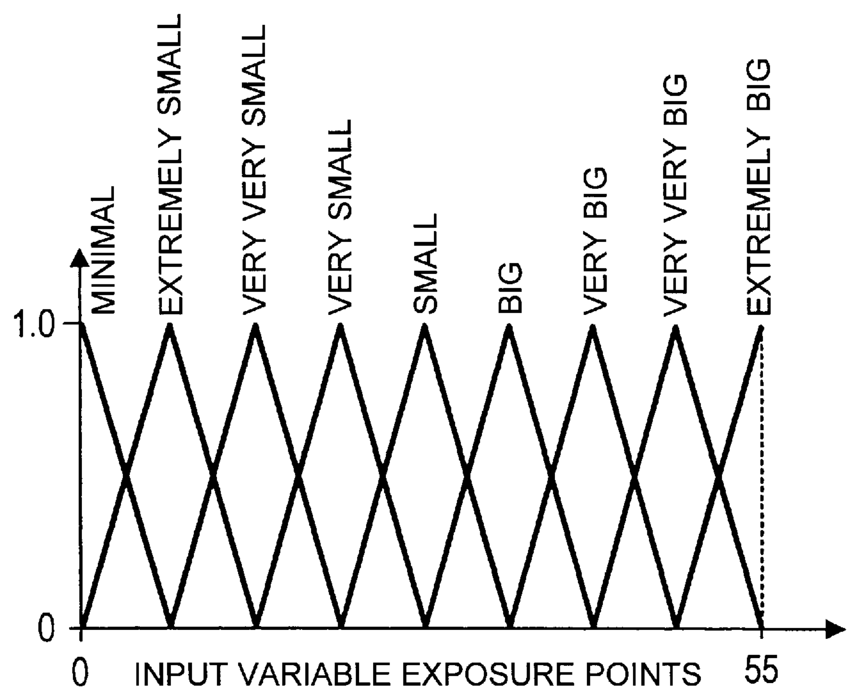
Figure 24:
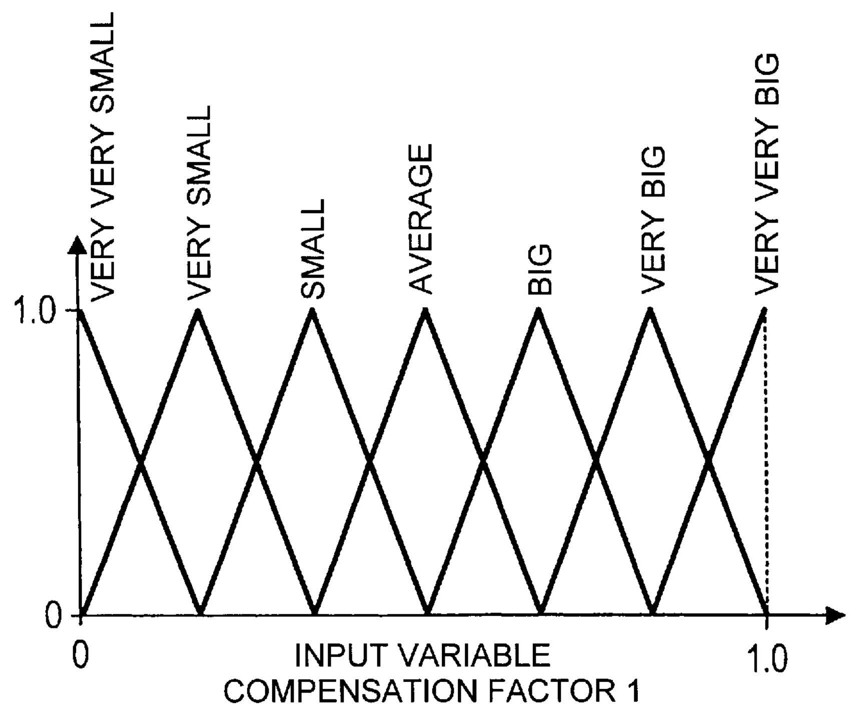
Figure 25:
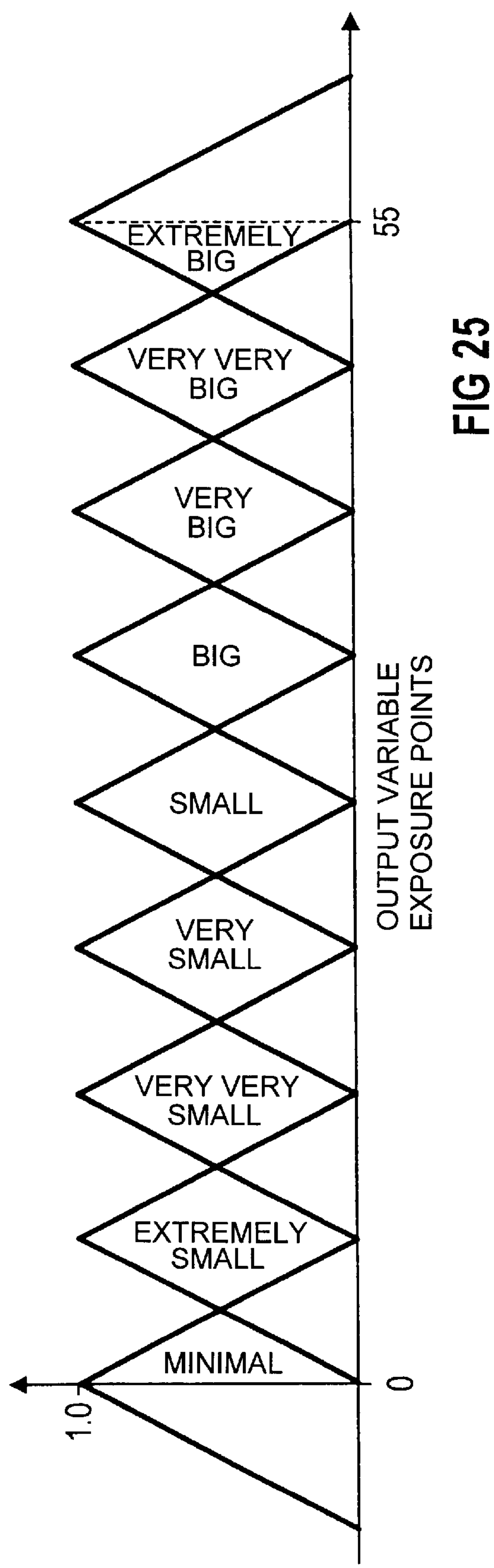

A second exposure point determination ensues in a sixth individual module 16 to which the first compensation factor, i.e. the output signal of the of the fourth individual module 14, ad the output signal of the third individual module 13 are supplied as exposure points. A second exposure point number is output as output parameters. The input fuzzy sets of the sixth individual module 16 are shown in FIGS. 23 and 24, the output fuzzy sets in FIG. 25 and the rule base in FIG. 26.

Figure 27:
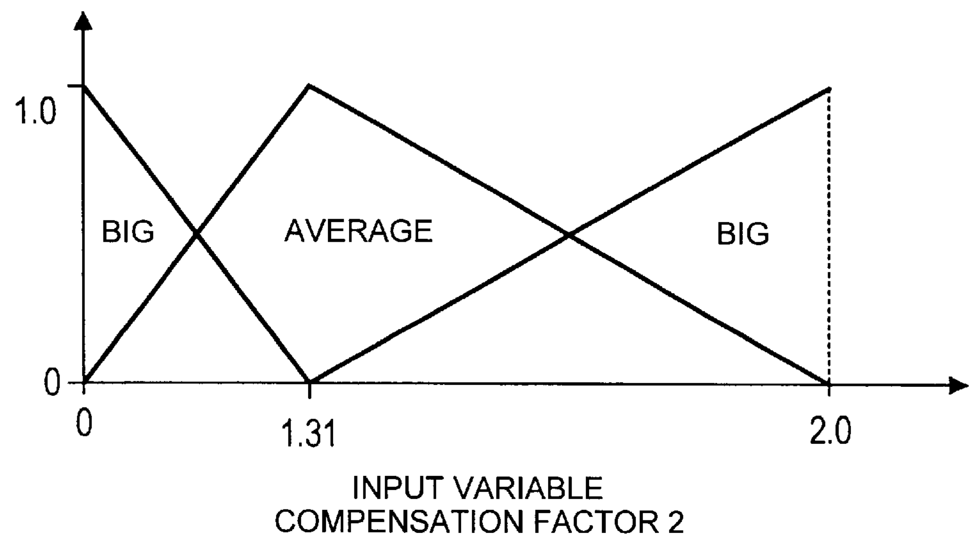
Figure 28:
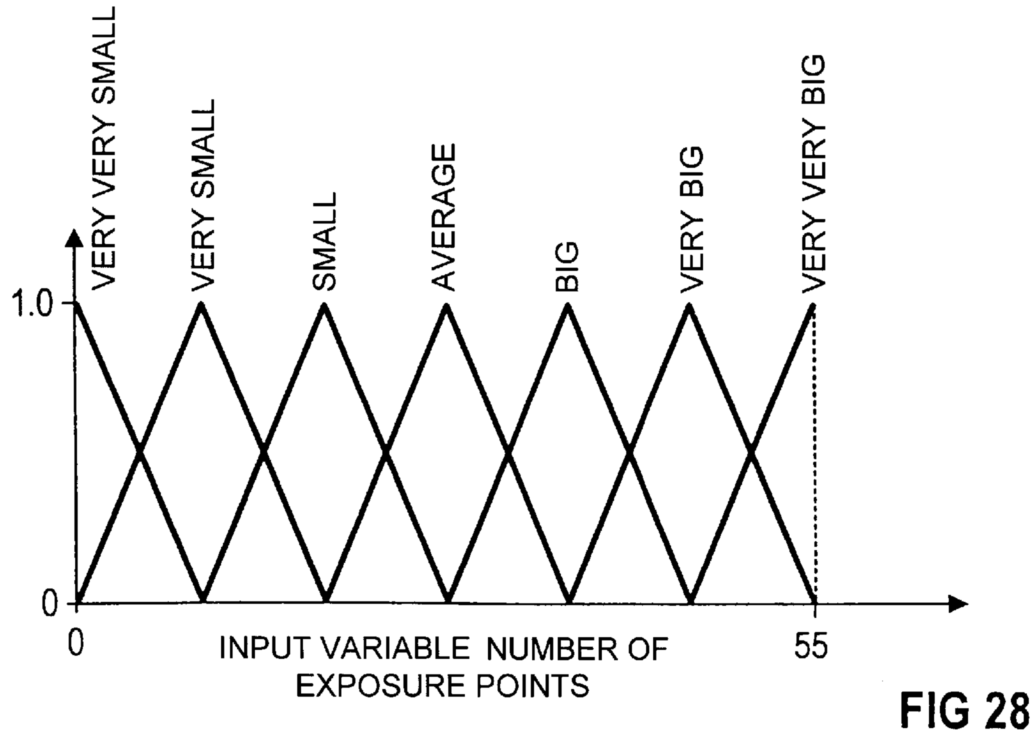
Figure 29:
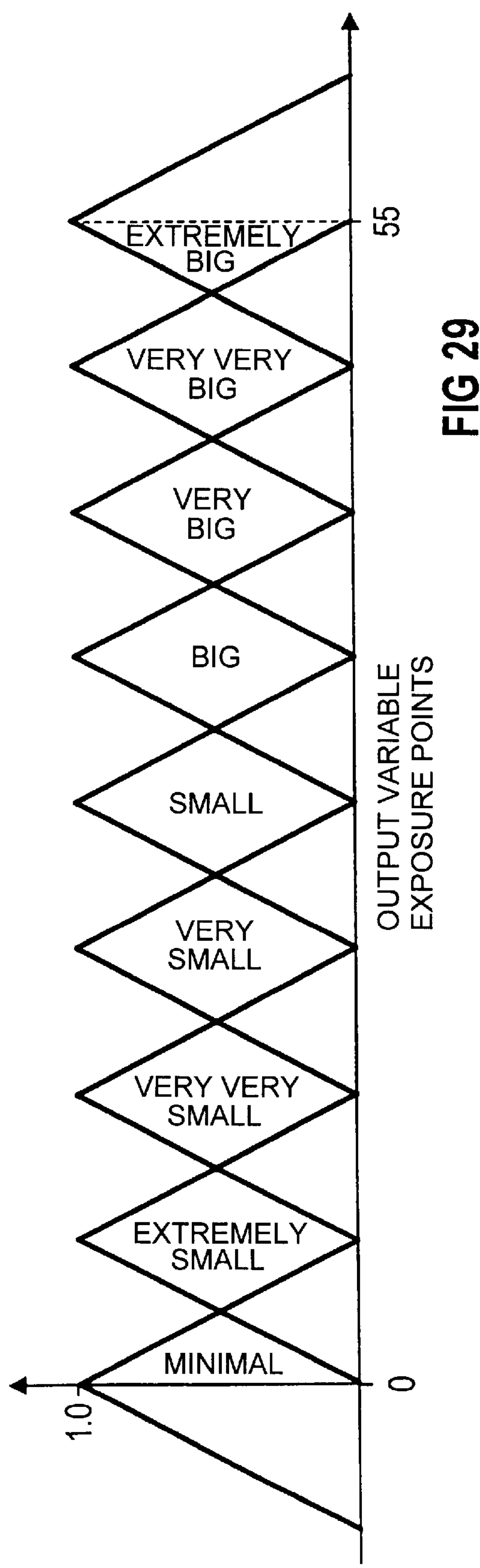

Finally, the second compensation factor, i.e. the output signal of the fifth individual module 15, and the second exposure point number, i.e. the output signal of the sixth individual module 16, are supplied to a seventh individual 17 as input parameters. A modification of the result of the second exposure point determination by the value of the compensation of the angulation ensues in the seventh individual module 17. The result is the output value of the fuzzy control system. The input fuzzy sets of the seventh individual module 17 are shown in FIGS. 27 and 28, the output fuzzy set is shown in FIG. 29 and the rule base is shown in FIG. 30.

Figure 31:
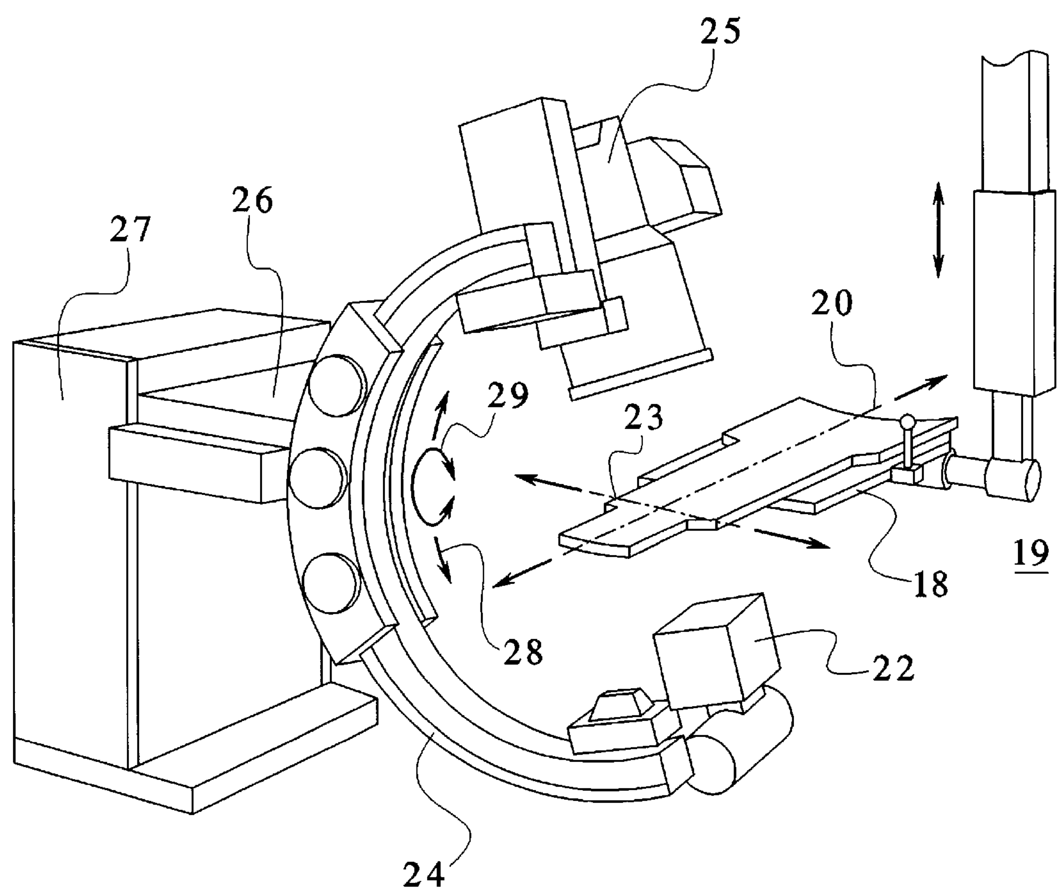
FIG. 31 is a perspective view of an exemplary embodiment of an X-ray diagnostics apparatus.

What is critical for the subject matter of the present invention is not the explained fuzzy control system for an X-ray diagnostics apparatus shown by way of example in FIG. 31. The structuring and modularization of a fuzzy system are critical to the invention in order, in particular, to simplify this in view of the rule bases to be written. As a result of the invention, the system behavior of a fuzzy system can be targeted and fashioned in a simple way according to predetermined ideas. A tedious testing of fuzzy set configurations can thus be eliminated. Moreover, the properties of existing fuzzy systems can be judged on the basis of the rule base and fuzzy sets. A simulation of the system is no longer necessary therefor.

A further improvement in view of the configuration of fuzzy sets derives with a closed algorithm. An automatic matching of fuzzy set and rule base is thus possible, this enabling the trainability of this fuzzy system.

Figure 8:
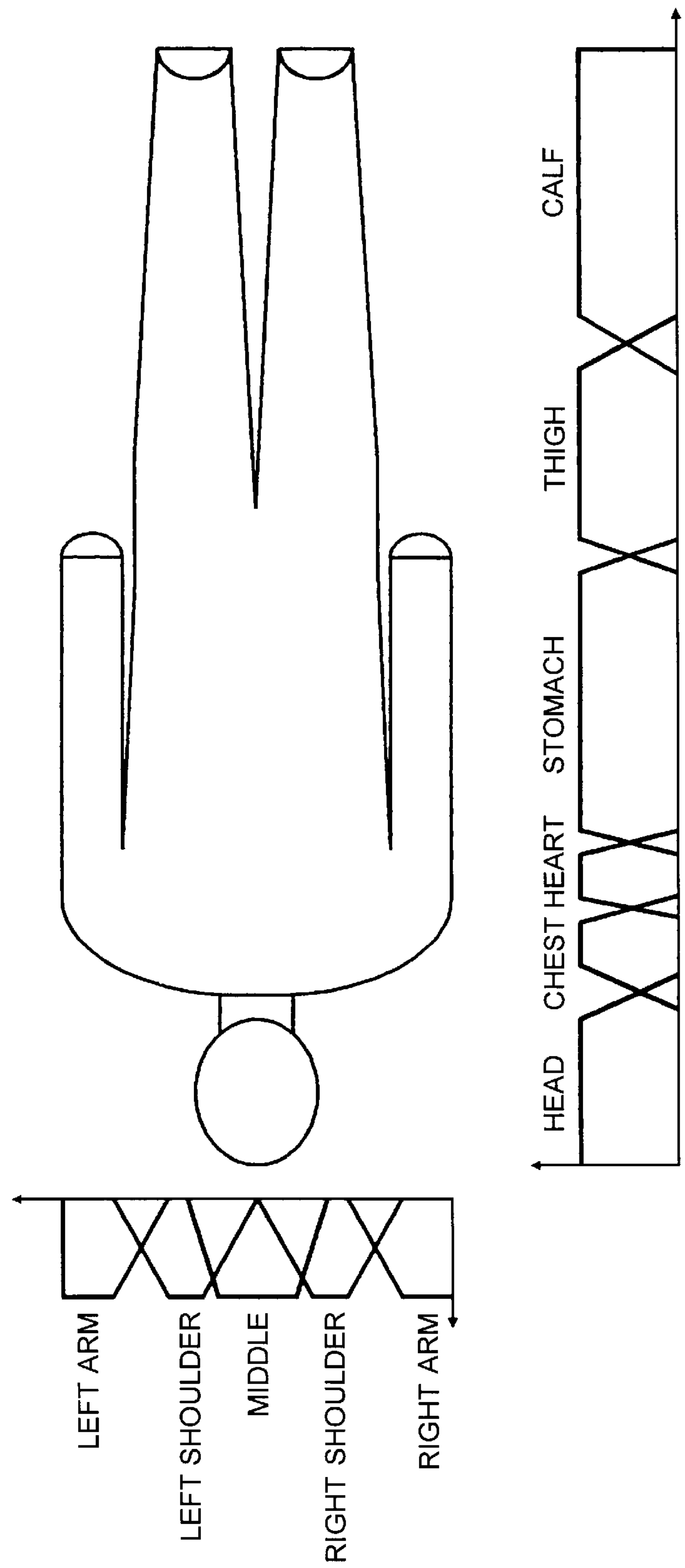
Figure 9:
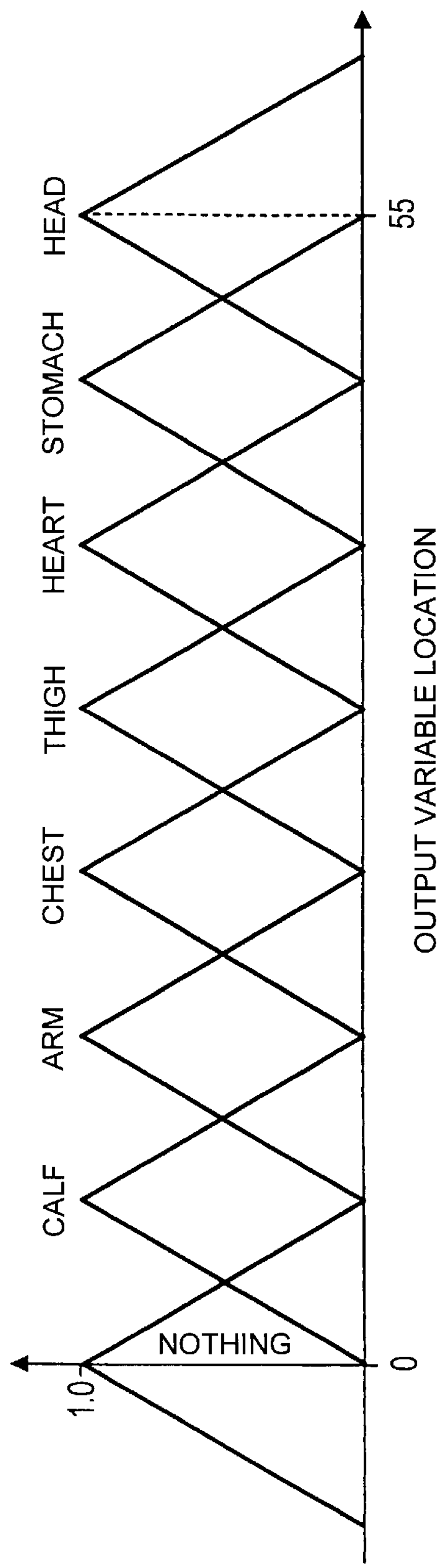

Given the exemplary embodiment of an X-ray diagnostics apparatus shown in FIG. 31, a bearing mechanism with a table 18 for bearing an examination subject 21, see FIG. 8, is identified with reference character 19. The table 18 is adjustable along its longitudinal axis 20, the X coordinate deriving therefrom. As already explained, the table positions are normed with the dimensions of the body of the examination subject 21. The X coordinate 0 means that the radiation transmitter 22 is located at the head of the examination subject 21. The X coordinate 1 means that the radiation transmitter 22 is located at the feet of the examination subject. The table 18 is adjustable along a transverse axis 23, the Y coordinate deriving therefrom. When the radiation transmitter 22 is located at the right side of the body of the examination subject 21, then the Y coordinate has the value 0 assigned to it and, when the radiation transmitter 22 is located at the left side of the body, then the value 1, for example, is allocated to the Y coordinate. It is shown that the radiation transmitter 22 is seated at an end of a C-bend 24, a radiation receiver 25 being arranged at the end thereof lying opposite the radiation transmitter 22. The C-bend 24 is adjustably seated at a base 27 via a holder 26. The holder 26 allows an adjustment of the C-bend 24 along its circumference, so that the pick-up unit composed of the radiation transmitter 22 and the radiation receiver 25 can be adjusted around an isocenter, for example by a rotational angle 28 from 0° through 360°. The rotational angle 28, also referred to as R-LAO, indicates the rotation of the C-bend 24 around the longitudinal axis 20 and is measured between the current position of the radiation transmitter 22 and the vertical. The holder 26 also allows a tilting of the pick-up unit around a tilting angle 29 that is referenced k—k and that indicates the rotation of the C-bend 24 around the transverse axis 23. The rotation of the radiation transmitter in the direction to the foot end is called cranial and that in the direction to the head is called caudal. The tilting angle relative to the head is measured with a negative angle and that relative to the feet is measured with a positive angle.

Within the scope of the invention, of course, the X-ray diagnostics apparatus can also be implemented with only a single radiation transmitter 22 that is adjustable at a holder.

Although other modifications and changes may be suggested by those skilled in the art, it is the intention of the inventors to embody within the patent warranted hereon all changes and modifications as reasonably and properly come within the scope of their contribution to the art.

We claim:

1. An X-ray diagnostics apparatus with a fuzzy control system for dose rate control, comprising:

a bearing mechanism for an examination subject;

an x-ray exposure unit;

means for determining start values for a dose rate control from signals specifying a type of examination subject; and means for representing one of a position of said bearing mechanism in a plane and an alignment of the exposure unit.

2. An X-ray diagnostics apparatus with a fuzzy control system according to claim 1, wherein said means for determining includes a first individual module, and further comprising:

means for supplying signals specifying the type of examination subject to an input of said first individual module.

3. An X-ray diagnostics apparatus with a fuzzy control system according to claim 2, wherein said first individual module includes first and second inputs, and further comprising:

means for supplying signals representing a weight of the examination subject to said first input of the first individual module and signals representing a size of the examination subject to said second input of said first individual module.

4. An X-ray diagnostics apparatus with a fuzzy control system according to claim 1, further comprising:

a second individual module having an input; and means for supplying signals representing the position of said bearing mechanism in a plane to the input of said second individual module for location classification.

5. An X-ray diagnostics apparatus with a fuzzy control system according to claim 4, further comprising:

a third individual module connected to receive an output signal of the first and second individual module for first exposure point determination.

6. An X-ray diagnostics apparatus with a fuzzy control system according to claim 5, further comprising:

a pick-up unit for x-rays; and a fourth individual module connected to receive an output signal of the second individual module and a signal corresponding to an angle of inclination of the pick-up unit of the X-ray diagnostic apparatus.

7. An X-ray diagnostics apparatus with a fuzzy control system according to claim 6, further comprising:

a fifth individual module connected to receive the output signal of the second individual module and a signal representing a rotational angle of the pick-up unit.

8. An X-ray diagnostics apparatus with a fuzzy control system according to claim 6, further comprising:

a sixth individual module connected to receive the output signal of the third and of the fourth individual module for a second exposure point determination.

9. An X-ray diagnostics apparatus with a fuzzy control system according to claim 8, further comprising:

a seventh individual module connected to receive an output signal of the fifth and of the sixth individual module, and an x-radiation transmitter;

means for controlling said radiation transmitter connected to receive an output signal of the seventh individual module.

* * * * *